United States Patent [19]
Jacobson et al.

[11] Patent Number: 4,908,322
[45] Date of Patent: Mar. 13, 1990

[54] DERIVATIZATION OF AMINES FOR ELECTROCHEMICAL DETECTION

[75] Inventors: Kenneth A. Jacobson, Silver Spring; Kenneth L. Kirk, Bethesda; Markku I. Linnoila, Bethesda; Thomas Miller, Bethesda; Kazunori Mine, Rockville, all of Md.

[73] Assignee: The United States of America as represented by the Department of Health and Human Services, Washington, D.C.

[21] Appl. No.: 290,279

[22] Filed: Dec. 27, 1988

Related U.S. Application Data

[63] Continuation of Ser. No. 773,069, Sep. 6, 1985, abandoned.

[51] Int. Cl.$^4$ .................... G01N 30/02; G01N 30/64; G01N 33/48
[52] U.S. Cl. .................... 436/111; 436/106; 436/112; 436/161; 436/816; 436/901
[58] Field of Search .................... 436/8, 106, 111-113, 436/116, 806, 816, 901

[56] References Cited

U.S. PATENT DOCUMENTS

| | | | |
|---|---|---|---|
| 4,288,547 | 9/1981 | Yamamoto | 435/809 X |
| 4,412,068 | 10/1983 | Rosi | 435/869 X |
| 4,430,263 | 2/1984 | March et al. | 436/500 X |

FOREIGN PATENT DOCUMENTS 1546068  6/1976  United Kingdom .

OTHER PUBLICATIONS

"Microdetermination of Hydrazine Salts & Certain Derivatives w/N-Chlorosuccinimide," *Anal. Chem.*, 46(6), pp. 777-779.

"Simultaneous Determination of Histamine and $N^\tau$-Methylhistamine With High-Performance Liquid Chromatography Using Electrochemical Detection," *Analytical Biochemistry*, 152, pp. 127-135.

CA 91:222032e, New Derivatization of Amines for Electrochemical Detection in Liquid Chromatography.

*Primary Examiner*—Barry S. Richman
*Assistant Examiner*—Jill Johnston

[57] ABSTRACT

Primary and secondary amines in biological fluids are selectively derivitized by reaction with esters of N-hydroxysuccinimide or N-hydroxysulfosuccinimide to form an N-acylated derivative. Those N-acylated derivatives may then be extracted into a polar organic phase and extracted. Non-electroactive amines may be made suitable for coulometric analysis by selecting the ester used so as to attach an electroactive group to the amine. For example, histamine may be reacted with the Bolton-Hunter reagent to form a suitable derivative in high yield.

25 Claims, No Drawings

DERIVATIZATION OF AMINES FOR ELECTROCHEMICAL DETECTION

This application is a continuation of application Ser. No. 773,069, filed Sept. 6, 1985, abandoned.

FIELD OF THE INVENTION

The present invention relates generally to the detection of amines in fluids and more particularly to the electrochemical quantitative detection of amines in biological fluids.

BACKGROUND OF THE INVENTION

Electrochemical detection coupled to high pressure liquid chromatography is a means for determining relative or absolute quantities of readily oxidizable materials in solution. The high sensitivity of the method makes it comparable to radioactive tracer methods for determination of minute quantities.

At the level of picomoles or less per sample the presence of a high concentration of salts, proteins, or other extraneous solutes may interfere with the detection. This is a problem particularly with biological fluids, which usually cannot be injected directly into a high pressure liquid chromatography (HPLC) column equipped with a coulometric detector. A preliminary separation procedure is desirable. This typically consists of column chromatography, perhaps involving an ion exchange resin. This separation increases the number of manipulations required per sample and complicates the rapid determination of a large number of samples.

Another limitation of current methodology is that the compound of interest must contain an electroactive (oxidizable or reducible) group such as a phenol group. Many components of interest in biological fluids cannot at present be measured by electrochemical detection, because they are not sufficiently electroactive. The biogenic amines, histamine, for instance, which is an important chemical messenger in the body and one of the mediators of anaphylactic reactions, are chemicals which cannot be detected directly. A chemical derivatization method for such non-electroactive amines, based on an o-phthalaldehyde reaction, has been suggested, but this approach suffers from a reversibility of the derivatization reaction and a low sensitivity.

SUMMARY OF THE INVENTION

It is an object of the present invention to provide a method for the analysis of fluids containing amines which overcomes the disadvantages of prior art methods.

It is another object of the present invention to provide a process for the analysis of fluids containing amines which does not require an overly burdensome number of manipulations per sample.

It is a further object of the present invention to provide a method for the coulometric detection of both electroactive and non-electroactive amines in biological fluids.

It is yet another object of the present invention to provide a method for the electrochemical quantitative detection of certain amines in fluids which had not previously been detectable by electrochemical methods.

The present invention is a novel approach to derivatization of amines for electrochemical detection, based on selective N-acylation. The class of acylating agents consisting of reactive o-acyl hydroxylamine derivatives, and particularly active esters of N-hydroxysuccinimide (compound 1 in Scheme 1), are known for:

(1) stability in aqueous medium,
(2) rapid and complete reactions with amines (compound 2 in Scheme 1), and
(3) selectivity of reaction towards amines versus other nucleophiles present, such as alcohols, and, in particular, phenols.

SCHEME 1

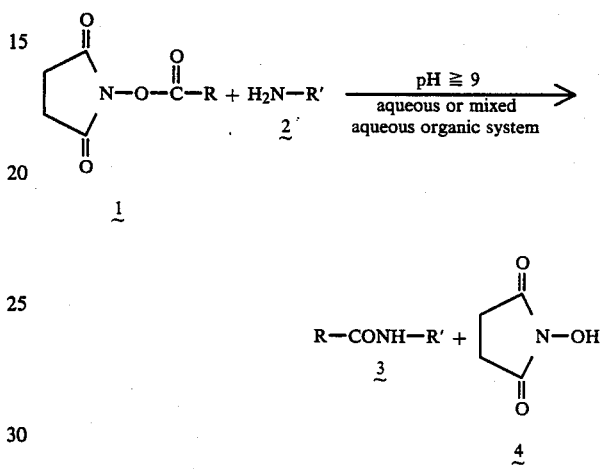

At neutral pH, small primary amines generally bear a positive charge and are too polar to be extracted into organic solvents. Acylation of the amine allows one to extract the now neutral derivative into an organic solvent (especially, but not exclusively, if there are no other charged groups on the molecule) leaving salts and proteins behind in the aqueous phase. Thus, acylation eliminates the need for a complicated, preliminary purification or isolation scheme based on columns. In addition, if a volatile organic solvent is used, the ability to concentrate the extract by evaporation increases the overall detection range.

N-hydroxysuccinimide esters are particularly advantageous for the purpose of the present invention as the derivatization reaction does not seriously diminish the electroactivity (oxidation or reduction potential) of most amines having a naturally occurring electroactive group. For example N-hydroxysuccinimide esters are not particularly reactive towards phenols. Thus, when using the present invention to detect phenolic amines, such as serotonin, the natural electroactivity of the compound which renders it easily detectable electrochemically is not affected by the derivatization reaction.

On the other hand, if the amine to be measured does not bear a readily electroactive group, such a group may be attached through the acylation reaction (see Scheme 2). Examples of oxidizable electroactive groups which may be attached through acylation for this purpose are: para-substituted phenols, hydroquinones, aniline derivatives, thiols and thioethers. Examples of reducible electroactive groups which may be attached through acylation for this purpose are quinones, nitroaromatics, and disulfides. For example, a single hydroxyl group on a phenyl ring is sufficient for highly sensitive detection by the electrochemical method. One bifunctional reagent to accomplish attachment of a substituted phenol to an amine lacking a readily electroactive group consists of N-hydroxysuccinimide esterified with a carboxyl group which is linked to the phenol, possibly through a chain or spacer group. An example of such a reagent, which conveniently is commercially available is N-succinimidyl-4-hydroxyphenyl propionate, frequently referred to as Bolton-Hunter reagent. This reagent is popular for radioiodinations of proteins via acylation. A general scheme for derivation according to the present invention is as follows:

SCHEME 2

Key

  oxidizable moiety (eg. phenol)

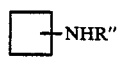  biogenic primary or secondary amine

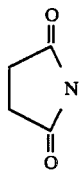  N—hydroxysuccinimide (active) ester (1) amines bearing oxidizable groups:

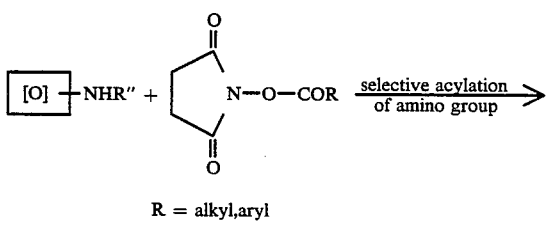

R = alkyl,aryl

↓ extraction into organic solvent (2) other amines:

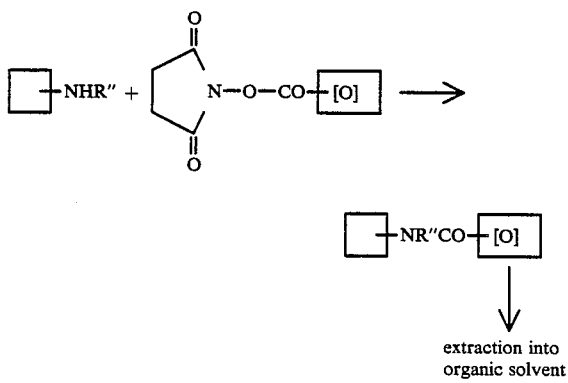

↓

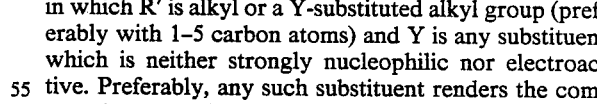

↓ extraction into organic solvent

Thus, the purpose of derivatization of a non-electroactive molecule is two-fold:

(1) to allow extraction of the amine-derived material into an organic phase, eliminating potentially interfering components, and/or (2) to add an oxidizable or reducible moiety to the molecule, thereby rendering it detectable electrochemically.

DETAILED DESCRIPTION OF THE PREFERRED EMBODIMENTS

The reactive o-acyl hydroxylamine derivatives usable as the acylating agent in accordance with the present invention may include any such derivative which is not reactive toward hydroxyl groups, such as on a phenol group, and whose nitrogen is not sufficiently nucleophilic towards acylation that it can itself be acylated under mild conditions. Examples of such o-acyl hydroxylamine derivatives usable in the present invention include:

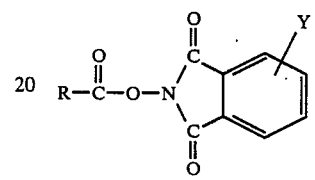 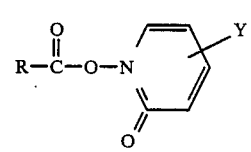

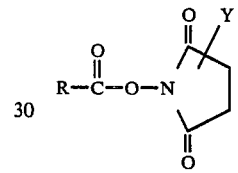 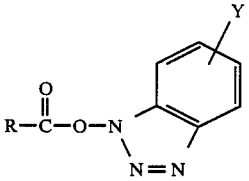

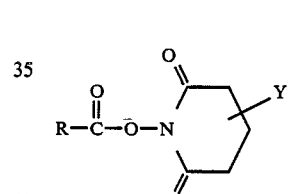 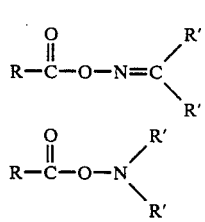

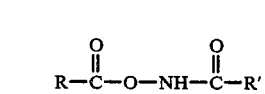 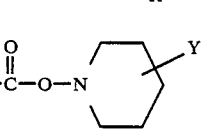

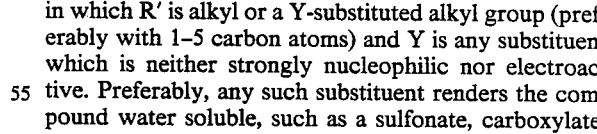 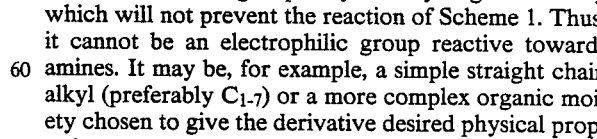

in which $R'$ is alkyl or a Y-substituted alkyl group (preferably with 1–5 carbon atoms) and Y is any substituent which is neither strongly nucleophilic nor electroactive. Preferably, any such substituent renders the compound water soluble, such as a sulfonate, carboxylate, urea, etc. The R group may be any organic moiety which will not prevent the reaction of Scheme 1. Thus, it cannot be an electrophilic group reactive towards amines. It may be, for example, a simple straight chain alkyl (preferably $C_{1-7}$) or a more complex organic moiety chosen to give the derivative desired physical properties.

The preferred acylating agents are the N-hydroxysuccinimide esters, including those in which the succinimide group is substituted with a Y group as discussed hereinabove. Most preferred are N-hydroxysulfosuccinimide esters. The latter compounds may be synthesized according to the method of Staros in *Biochemistry*, vol 21, 3950-55 (1982).

When the acylating agent is not completely soluble in water, a co-solvent such as dioxane or methanol, may be necessary to increase solubility. Furthermore, at the end of the derivatization reaction, there are unreacted and unhydrolyzed active esters remaining. If the reagent is extractable into the organic phase along with the acylated amine, such as in the case of unsubstituted N-hydroxysuccinimide esters, a quenching agent, such as a simple amino acid, may be added at the end of the reaction.

The use of co-solvents and quenching agents is not necessary when using water soluble acylating agents, such as N-hydroxysulfosuccinimide esters. The latter esters are infinitely soluble in aqueous medium and excess acylating agent remains in the aqueous layer. Lower temperatures and shorter reaction times also result from the use of N-hydroxysulfosuccinimide esters.

Throughout the remainder of the present specification, N-hydroxysuccinimide esters or N-hydroxysulfosuccinimide esters will be discussed as the acylating agents of the present invention. It should be understood, however, whenever these specific agents are discussed, that other o-acyl hydroxylamine derivatives as defined above may also be used.

Two classes of amines which may be measured in biological fluids through derivatization by o-acyl hydroxylamine derivatives, such as N-hydroxysuccinimide esters (or their sulfo analogs), are discussed below. The classes are distinguished by the presence or absence of an electroactive group in the native state. Compounds of both classes must have a single nucleophilic primary or secondary amino group to participate in the acylation reaction.

(1) Determination of amines already bearing electroactive groups.

Biological amines which are electroactive (for example, the catecholamines) may be measured through their N-acyl derivatives formed using N-hydroxysuccinimide esters. The added acyl group (—COR of Scheme 2) may contain a simple straight chain alkyl group (e.g. acetyl, propionyl, etc.) or may contain more complex organic moieties chosen to give the derivatives desired physical properties. Which acyl group is used will influence the hydrophobicity of the derivative and thus the retention time on high pressure liquid chromatography. Using an aqueous mobile phase and a stationary phase of organic bonded silica, the retention time will be increased with increasing size of the alkyl group. Thus, amines which are highly polar in the native state, may be made considerably less polar by binding a sufficiently hydrophobic R group. On the other hand, amines which are highly hydrophobic, and their simple N-acyl derivatives have too high an affinity for the column packing resulting in long retention times and peak broadening, are best derivatized using hydrophilic R groups. An example of an N-hydroxysuccinimide ester which would donate an uncharged hydrophilic moiety to the amine is the glycine derivative:

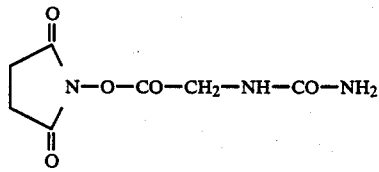

This versatility of being able to vary the polarity of the N-acylated derivative facilitates the selection of suitable chromatographic conditions for a particular amine.

The acylation approach has been used successfully for the detection of electroactive biogenic amines in biological samples from hospitalized normal and abnormal volunteers. A representative example of serotonin determination is described. Serotonin (5-hydroxytryptamine) is a neutrotransmitter found in the central nervous system and in various peripheral organs. The turnover of serotonin in various parts of the brain is believed to be related to behavior and has been correlated to sleep states. Abnormal serotonin metabolism has been implicated in mental disorders.

Serotonin (compound 7 in Scheme 3) reacts with N-succinimidyl acetate (8) selectively on the primary alkyl amine, as shown below, to give N-acetylserotonin (9). The electroactive hydroxytryptamine ring system emerges from the reaction unchanged. In practice a biological sample of 1.0 ml volume (for example: cerebrospinal fluid) is degassed by bubbling argon and treated with 0.05 ml of a solution of N-succinimidyl acetate in dioxane (100 mg/ml). The reaction is carried out at a pH of 10-11 in a closed vessel under argon at 70° C. for a period as short as five minutes or as long as two hours. The reaction is then quenched with glycine, giving the non-electroactive sodium N-acetylglycinate (10).

Scheme 3

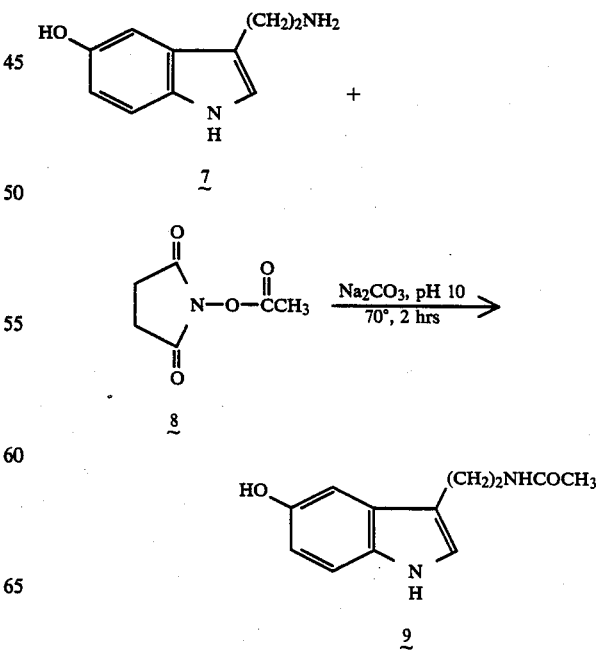

Scheme 3 -continued

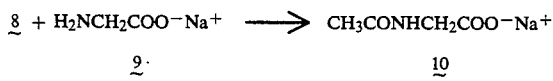

Upon extraction of the aqueous reaction mixture with ethyl acetate, only the non-polar constituents such as N-acetylserotonin are removed. This derivative is measurable by HPLC using a coulometric detector (chromatographic conditions specified in Table 1). Since biological extracts such as cerebrospinal fluid, contain other acylatable amines, such as tyramine, these derivatives are also extracted in the process. Other N-acetylamines, however, do not interfere with serotonin determination since they are generally separable from N-acetylserotonin by HPLC. Moreover, using the appropriate chromatographic conditions and internal standards they may be determined concurrently with serotonin.

Samples which are believed to contain native N-acetylserotonin may be treated similarly with N-succinimidyl propionate or another ester similar to the acetate. N-Propionylserotonin is less polar than N-acetylserotonin and the two may be separated by HPLC. Thus, in a single derivatization reaction and injection on HPLC both serotonin (as the N-propionyl derivative) and endogenous N-acetylserotonin may be determined.

Alternately, samples containing serotonin may be treated with hydroxy sulfosuccinimidyl esters, such as N-(hydroxy sulfosuccinimidyl) acetate (compound 11 in Scheme 4), to produce the identical derivatives. Advantages of the sulfo analogs are that an organic cosolvent is not required, and quenching is not necessary. Generally, overall yields with the soluble sulfo active esters are more favorable.

Scheme 4

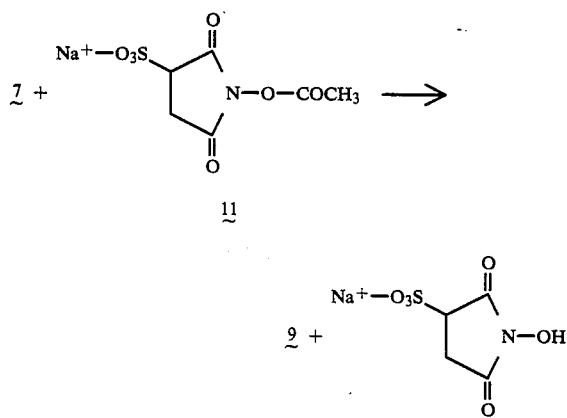

Serotonin derivatives, such as 5-hydroxytryptophanol (compound 13 of Scheme 5), and the series of N-alkyl amides of 5-hydroxytryptophan (14) which are of similar reactivity and sufficiently stable under the acylation conditions, may be added as internal standards. The internal standards are added to biological samples to correct for incomplete reaction, losses in oxidation, etc. Compounds 13 and 14 are synthesized in one step (lithium borohydride reduction or aminolysis, respectively) from commercially-available 5-hydroxytryptophan ethyl ester. The advantage of using derivatives such as compound 14 as internal standards is that the alkyl group is easily varied to alter the retention time. Having a series of internal standards from which to choose overcomes the problem of interfering peaks in the HPLC. The variation of compound 14 in which the alkyl group is ethyl is a convenient internal standard in the determination of serotonin using N-succinimidyl propionate; the retention time of N-propionyl serotonin is two minutes longer than the retention time of the N-propionyl derivative of 5-hydroxytryptophan ethylamide under conditions specified in Table 1.

Scheme 5

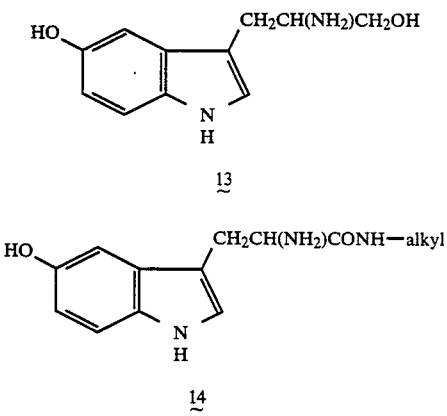

By the method outlined above, serotonin has been determined with a sensitivity limit as low as 0.1 picomoles per sample. Thus, the method is highly sensitive, even in comparison to other HPLC derivatization schemes such as fluorescamine. This degree of sensitivity permits the determination of amines in biological samples of small volume, such as biopsy tissue samples.

Other electroactive amines, such as catecholamines, are determined in a similar manner using N-succinimidyl propionate as the acylating agent. Following the reaction, the N-propionyl derivatives as listed in Table 1 are extracted quantitatively from acidic, aqueous solution into ethyl acetate or other appropriate immiscible organic solvent. It can be seen from Table 1 that the retention time differs for each parent amine. Thus, the method may be used to quantitatively detect more than one amine in the same run.

TABLE 1

Properties of N—propionyl derivatives of biogenic amines.

| parent amine | ion observed in mass spectrum[a] | retention time[b] |
|---|---|---|
| dopamine | 210[c] | 9.2 min |
| epinephrine | 222[d] | 9.0 |
| metanephrine | 236[d] | 19.3 |
| 3-methoxytyramine | 214[c] | 23.4 |
| norepinephrine | 208[d] | 3.3 |
| normetanephrine | 222[d] | 6.0 |
| octopamine | 210[c] | 4.6 |
| serotonin | 233[c] | 17.6 |
| tyramine | 194[c] | 17.0 |

[a] chemical ionization with ammonia gas.
[b] mobile phase: sodium acetate buffer (0.1 M, pH 4.8) containing 6.3% acetonitrile, 2.3% methanol, and 0.01% EDTA; column: Supelco RP, LC-8, 3 micron particle size, 4.6 mm × 15 cm; flow 1.3 ml/min, 3500 psi.
[c] equals molecular weight +1
[d] equal molecular weight −18 + 1, due to elimination of water.

(2) Determination of amines not bearing an electroactive group.

Tryptamine, histamine, and other non-electroactive amines in biological samples are derivatized with electroactive groups through N-acylation.

Histamine in minute quantities in biological samples reacts with Bolton-Hunter reagent (compound 16a in Scheme 6) or its sulfo analog (compound 16b) to form compound 17 in high yield (80–90%). The reaction conditions are similar to those described for acylation of electroactive amines. The optimal pH for the reaction is 10. After quenching with glycine, the hestamine derivative bearing a phenol (17) may be extracted into relatively polar immiscible organic solvent mixtures, such as n-butanol or ethyl acetate/acetonitrile. The p-hydroxyphenylpropionic acid formed from hydrolysis of excess acylating reagent is removed by a prior extraction from acidic solution into a less polar organic solvent. Alternately, the derivative may be separated from the reaction mixture by binding to a weak cation exchange resin (Celex-P) followed by elution with dilute HCl. When the acylating agent is the water soluble sulfo analog of the Bolton-Hunter reagent (16b) the reaction occurs efficiently and to completion (yield typically 90%) at room temperature for twenty minutes with vigorous shaking. The N-propionyl derivative of histamine is measurable by electrochemical detection using a BSA or ESA detector. A linear response to histamine added in known concentrations to the sample subjected to acylation is obtained in the range of tenths of picomoles and above.

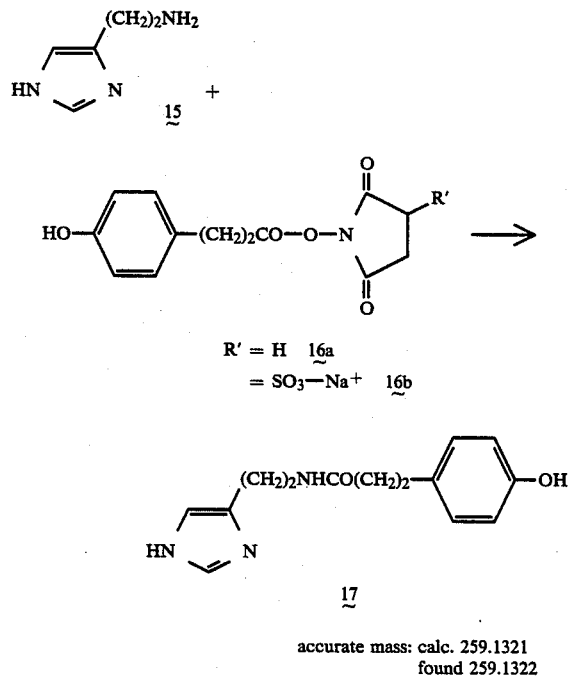

Scheme 6

Nτ-methylhistamine may be detected similarly via derivative 18 (Scheme 7), which is separable by HPLC from the analogous derivative of histamine. Histidinol or Nα-methylhistamine (19) may be used as internal standards of similar reactivity to the naturally-occurring histamines but of slightly different polarity. Thus, the products, compounds 20 and 21, respectively, may be separated from other histamine-related derivatives such as 18 by HPLC. Compound 21, but not compound 20, is compatable with the Celex-P ion exchange column procedure mentioned above, due to the low $pK_a$ of the imidazolium form of 20.

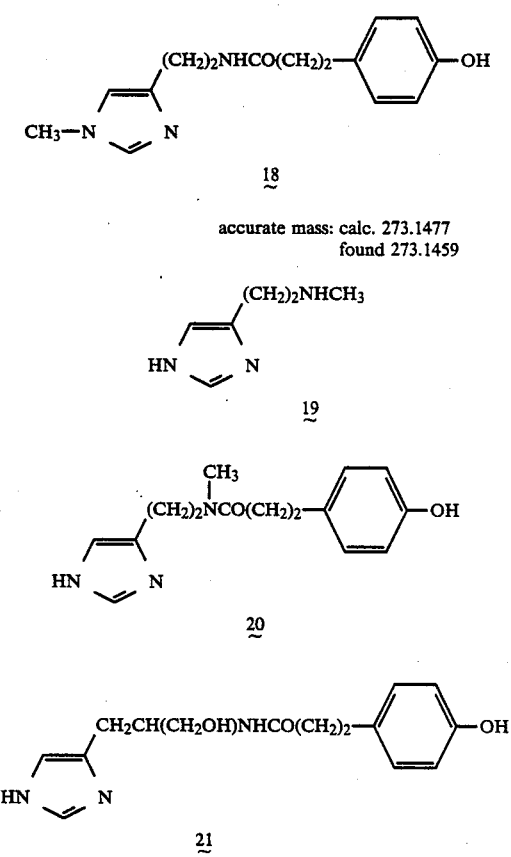

Scheme 7

Non-electroactive amines which are less polar than histamine may be measured quantitatively by derivatization with the Bolton-Hunter reagent or its sulfo analog, and the derivatives extracted into an organic solvent, such as ethyl acetate. This obviates the need for column chromatographic purification prior to HPLC, as required for histamine determination. Examples of amines detectable in this manner are p phenylethylamine (using β-tolylethylamine as internal standard), tryptamine, and the commercial drugs tuamine, wyamine, and tranylcypromine.

The methods described above are designed for general application and are also useful for determining other amines, for example, phenylethylamine (non-electroactive, a metabolite of which was recently proposed as a clinical marker for mentally depressed states); drugs (such as tuamine, wyamine, tranylcypromine, amphetamine and mescaline) and drug metabolites bearing unhindered amino groups. Also, some peptides which do not contain electroactive residues in the native state, potentially may be derivatized for detection at the amino terminus. Conceivably, the method could be adapted to an automated instrument for carrying out determination of amines present at low levels. The sensitivity and reproducibility of the analyses may benefit also from a recently reported technique for increasing the responsiveness of the glassy carbon electrode to phenols.

EXAMPLES

Having fully described the invention above, the following examples are illustrative only and are not intended to limit the invention in any manner:

EXAMPLE 1

Serotonin

N-Succinimidyl acetate

N-Hydroxysuccinimide (17.33 g, 0.5 mol) was suspended in 120 ml tetrahydrofuran and cooled in an ice bath. Acetic anhydride (16 ml, 0.17 ml) and then triethylamine (22 ml, 0.16 mol) were added slowly. A solution formed, and then gradually a white precipitate appeared. After one half hour an equal volume of petroleum ether was added, and the crystalline product was collected. Yield 21.22 g (90%, mp 128°–130° C., lit. 15 mp 131°–132° C.). Analysis ($C_6H_7NO_4$): calc. 45.87% C, 4.49% H, 8.91% N; found 45.86%, C, 4.31% H, 8.61% N.

N-Succinimidyl propionate

N-hydroxysuccinimide (32.06 g) was suspended in ethyl acetate (150 ml). Propionic anhydride (37 ml) and triethylamine (39 ml) were added alternately in small portions. A solution formed and the vessel became warm as the reaction progressed. After cooling to room temperature, several milliliters of saturated saline were added, resulting in the precipitation of a thick crystalline mass (triethylammonium propionate). The solid was filtered and washed with ethyl acetate. The combined filtrate was washed with saturated saline (3×) and water (1×). Evaporation of the organic layer left a residue of oil, which crystallized upon scratching with a glass rod and trituration with petroleum ether to give 45.36 g of product (95.2% yield). Mp. 44°–46° C., analysis ($C_7H_9NO_4$); calc. 49.62% C, 5.30% H, 8.18% N; found 49.29% C, 5.20% H, 8.19% N.

5-Hydroxytryptophan ethylamide

5-Hydroxytryptophan ethyl ester hydrochloride (69 mg, obtained from Sigma Chemical Co.) was dissolved in 0.5 ml of a 70% aqueous solution of ethylamine (obtained from Aldrich Chemical Co., Inc.) and heated on a steam bath at 60° C. under argon for twelve hours. The solvent was evaporated under a stream of argon. The resulting oil was dissolved in methanol/ether and acidified with gaseous HCl. Insolubles were allowed to precipitate and the solvent decanted. The hydrochloride salt of the product (40 mg) was dried under high vacuum. Mass spectroscopy (CI-$NH_3$) showed a parent ion at 247 mass units (m+1).

Derivatization Procedure 1.0 ml of cerebrospinal fluid(CSF) of a test solution containing serotonin (5-HT) and acetyl 5-HT was placed in a 16×25 mm screw cap culture tube which had been exhaustively silanized. The solution was degassed for 5 mins. under a stream of argon. 50 microliters of N-succinimidyl propionate (220 mg per 1.0 ml p-dioxane) and 100 microliters of saturated $Na_2CO_3$ were added and after vortexing, argon degassing was resumed for 5 mins. The tube was capped; vortexed and incubated for 2 hours at 70° C. After which the reaction was quenched by adding 100 microliters of glycine (75 mg per 1.0 ml made pH 9.7 with NaOH) and agitation at room temperature on a mechanical shaker for 10 mins.

Extraction

The derivatization product was extracted twice with 3.0 ml of ethyl acetate which had been passed over aluminum oxide immediately prior to use. The column packing was renewed every three days. Extraction was done by vortexing for 30 sec. and centrifuging for 10 mins. The combined extracts were evaporated under argon in a silanized tube placed in a 37° C. water bath. The derivatized product was redissolved in 1.0 ml of argon degassed water, vortexed for 10 secs. and 100 microliters injected into the HPLC column.

Chromatography

High pressure liquid chromatography (HPLC) was done under isocratic conditions using a Model 6000 A pump (manufactured by Waters Associates) and U6K injector or Altex 210 injector. The column was a 15 cm×4.6 mm Supelco LC-8, 3 micron particle size. The running solvent was prepared daily as follows: 0.08M sodium acetate which was 2.3 and 6.3% (v/v) in methanol and acetonitrile, respectively, was adjusted to pH 4.8 with glacial acetic acid and then filtered under vacuum through a 0.45 micrometer type HA millipore filter. It was further degassed with stirring for 10 mins. The flow rate was 1.3 ml/min., which resulted in back pressure of 3500–3600 psi. An ESA Coulochem 5011A electrochemical detector with applied voltage setting 0.30 v. versus Ag/AgCl and an LKB chart recorder were used.

Precision and Accuracy

Artificial CSF was made in deionized water as follows: $NaH_2PO_4$ 0.5 mM, $Na_2HPO_4$ 0.25 mM, $MgCl_2$ 0.4 mM, $CaCl_2$ 0.65 mM, KCl 3.0 mM, NaCl 128 mM, $NaHCO_3$ 25 mM human serum albumin 250 mg per liter. Three concentrations of 5-HT and acetyl 5-HT were prepared and 6 ml portions frozen in silanized glass tubes and stored at 70° C. On each of 5 days, one tube of each concentration was thawed and assayed in five 1.0 ml portions for a total of 15 reactions. In addition 30 1 ml portions at a single concentration were assayed in the same tubes in which they were frozen on each of 30 days. The peaks due to acetyl 5-HT and propionyl 5-HT were identified by comparison with authentic standards. The retention times were around 9 and 17 mins. respectively. No propionyl 5-HT peak was observed when 5-HT was absent from the derivatization reaction. Standard curves were run daily and were linear as long as dilutions were done in silanized glass tubes. The results shown in Tables 2 and 3 were expressed as theoretical yields on interpolating from daily standard curves using the artificial CSF. Table 4 shows actual measured quantities fo serotonin in cerebrospinal fluid of monkeys, using the above method.

The limit of sensitivity using human CSF is 0.1 picomol/ml CSF. This corresponds to 18 parts per trillion detection limit.

TABLE 2

| | Within Run Precision with Artificial CSF | | |
|---|---|---|---|
| Conc. ($\times 10^{10}$) | % Recovery M/l | Mean ± S.D. | % Cv* |
| 4 | 68.6 | 68.6 ± 4.03 | 5.87 |
| | 68.6 | | |
| | 62.9 | | |

TABLE 2-continued
Within Run Precision with Artificial CSF

| Conc. (× 10¹⁰) | % Recovery M/l | Mean ± S.D. | % Cv* |
|---|---|---|---|
| | 74.3 | | |
| | 68.6 | | |
| 10 | 98 | 58.7 ± 22.2 | 37.8 |
| | 50 | | |
| | 43.2 | | |
| | 50 | | |
| | 52.3 | | |
| | Acetyl 5-HT | | |
| 4 | 78.3 | 64.32 ± 14.9 | 23.2 |
| | 52.2 | | |
| | 56.5 | | |
| | 52.2 | | |
| | 82.6 | | |
| 10 | 61.4 | 47.74 ± 8.25 | 17.3 |
| | 47.4 | | |
| | 42.1 | | |
| | 40.4 | | |
| | 47.4 | | |
| | 5-HT | | |
| 4 | 52.4 | 4.95 ± 5.40 | 10.9 |
| | 57.1 | | |
| | 47.6 | | |
| | 47.6 | | |
| | 42.9 | | |
| 10 | 30.8 | 34.62 ± 4.69 | 13.56 |
| | 30.8 | | |
| | 40.4 | | |
| | 36.5 | | |
| | Acetyl 5-HT | | |
| 4 | 42.3 | 42.28 ± 4.74 | 11.2 |
| | 38.4 | | |
| | 42.3 | | |
| | 50.0 | | |
| | 33.4 | | |
| 10 | 47.1 | 39.70 ± 6.38 | 16.1 |
| | 40.0 | | |
| | 30.8 | | |
| | 47.7 | | |
| | 36.9 | | |
| | 5-HT | | |
| 4 | 84.8 | 70.30 ± 11.0 | 15.6 |
| | 78.8 | | |
| | 60.6 | | |
| | 60.6 | | |
| | 66.7 | | |
| 10 | 53.7 | 61.48 ± 11.4 | 18.5 |
| | 51.2 | | |
| | 56.1 | | |
| | 78.1 | | |
| | 68.3 | | |
| | Acetyl 5-HT | | |
| 4 | 53.6 | 48.78 ± 4.88 | 9.99 |
| | 43.9 | | |
| | 43.9 | | |
| | 48.8 | | |
| | 53.7 | | |
| 10 | 48.5 | 50.95 ± 2.94 | 5.78 |
| | 52.4 | | |
| | 48.5 | | |
| | 54.4 | | |
| | 5-HT | | |
| 1 | 50 | 50 + 17.7 | 35.3 |
| | 25 | | |
| | 50 | | |
| | 50 | | |
| | 75 | | |
| 4 | 64.7 | 45.28 + 13.4 | 29.6 |
| | 52.9 | | |
| | 41.1 | | |
| | 35.3 | | |
| | 32.4 | | |
| 10 | 39.3 | 27.62 ± 7.62 | 27.6 |
| | 28.6 | | |
| | 21.4 | | |
| | 20.2 | | |
| | 28.6 | | |
| | Acetyl 5-HT | | |
| 10 | 26.9 | 17.12 ± 6.12 | 35.7 |
| | 14.4 | | |
| | 10.6 | | |
| | 15.4 | | |
| | 18.3 | | |
| | 5-HT | | |
| 4 | 40 | 45 ± 3.54 | 7.8 |
| | 45 | | |
| | 45 | | |
| | 50 | | |
| | 45 | | |
| 10 | 40 | 41 ± 6.63 | 16.2 |
| | 46 | | |
| | 32 | | |
| | 46 | | |
| 4 | 36 | 39.2 ± 3.35 | 8.5 |
| | 44 | | |
| | 40 | | |
| | 36 | | |
| | 40 | | |
| 10 | 40.3 | 43.9 ± 5.73 | 12.1 |
| | 43.5 | | |
| | 51.6 | | |
| | 40.4 | | |

*CV (coefficient of variation) = 100 × (SD/mean)

TABLE 3
Between Run Precision in Artificial CSF

| Conc. (M/l × 10¹⁰) | N | % Recovery (Mean ± S.D.) | % Cv |
|---|---|---|---|
| | | 5-HT | |
| 1 | 5 | 50 ± 17.7 | 35.3 |
| 4 | 25 | 55.74 ± 13.90 | 25.0 |
| 10 | 23 | 45.28 ± 18.12 | 40.0 |
| | | Acetyl-5HT | |
| 4 | 20 | 48.65 ± 12.56 | 25.8 |
| 10 | 23 | 39.23 ± 13.72 | 34.9 |

TABLE 4
Results of analysis of monkey cerebrospinal fluid: (expressed in picomoles per ml cerebrospinal fluid)

| Analysis no. | Monkey | Endogenous N—Acetylserotonin | Serotonin (measured as N—propionyl derivative) |
|---|---|---|---|
| 1 | A29 | 0.72 | 0.24 |
| 2 | I36 | 3.1 | 0.5 |
| 3 | T7 | 2.1 | 0.36 |
| 4 | Chico (depinealized) | 0.2 | 0.45 |

Example 2

Histamine

Preparation of Tissue for Analysis

Rat brains were quickly removed after decapitation and the hypothalami were subsequently dissected. They were immediately frozen and weighed. The whole or a portion of the tissue were homogenized with 0.6 ml of ice cold 3% perchloric acid in a glass homogenizer. The homogenizer was rinsed three times with 0.5 ml of 3% perchloric acid. The homogenizer was rinsed three times with 0.5 ml of 3% perchloric acid. The homogenate and rinses were combined and an appropriate amount of Nα-methylhistamine solution was added as an internal standard. Then the sample was centrifuged at 10,000 g for 30 min. at 4° C. Prepurification of the extract was then performed. Dowex 50 W, dry wash 100–200 (Sigma) cation-exchange resin was washed sequentially with excess 2M hydrochloric acid, water, 2M sodium hydroxide and water. The washed resin was equilibrated with 0.2M sodium phosphate buffer, pH 6.5 and packed into a glass column (5 mm i.d.×16 mm). The supernatant of the tissue sample was directly poured into the column without adjusting its pH. After the column was washed with 5 ml of water and 4 ml of 2M hydrochloric acid, the amines were eluted with 3.5 ml of 3.5M hydrochloric acid. The first 1 ml fraction was discarded and the following 2.5 ml was collected into a silanized glass tube and evaporated to dryness.

Derivatization Procedure

The dry sample was dissolved in 0.8 ml of water and 150 ml of reaction buffer and 100 ml of 0.2M sulfo analog of Bolton-Hunter reagent (sulfo B-H) was added. To produce standards, 150 μl of reaction buffer and 100 μl of 0.02M sulfo B-H was added to one ml of standard solution with known quantities of histamine and Nτ- and Nα-methylhistamine. The pH of the mixture was between 9.8 and 10.0 when the evaporation of the hydrochloric acid was complete. The samples were shaken vigorously for 30 seconds using a vortex mixer (manufactured by Scientific Products). The derivatives were extracted using a cellulose phosphate fibrous cation-exchanger (Sigma) packed into a glass column (17 mm i.d.×13 mm) which was sequentially washed with excess 1M sodium hydroxide, water, 1M hydrochloric acid and finally with enough water to reach a pH between 5 and 6. The reaction mixture was then adjusted to pH 5.5 to 6.0 with 0.1M hydrochloric acid and applied to the column. The column was washed with 5 ml of water and 3 ml of 1 mM hydrochloric acid. The derivatives were eluted with 1.5 ml of 0.1M hydrochloric acid. The eluate was evaporated and stored at 4° C. in the dark, until HPLC analysis. Methanol was added to the dry sample followed by water to a final volume of 110 μl to 1 ml of 10% methanol solution. 100 μl of the solution was injected into the HPLC system.

Chromatography

The mobile phase consisted of a mixture of 0.14M sodium acetate and methanol (17:73 v/v) containing 3.89M 1-octane sulfonic acid and 56 mg of EDTA. The pH of the mobile phase was adjusted to 3.48 by adding glacial acetic acid. The mobile phase was degassed under vacuum before use. The flow rate through the HPLC column was 1.0 ml per minute. The chromatography was performed at room temperature. The electrochemical detector was operated in the oxidative screen mode using a response time of 10 sec. The potential of flow cell #1 was 0.47 V. Quantitation was accomplished in flow cell #2 at a potential of 0.56 V.

To determine the reaction yield for the amines with sulfo B-H, peak heights of standard amines after derivatization corresponding to 100 picomoles were compared with those of 100 picomoles of pure derivatives. Pure derivatives were made as follows. Histamine dihydrochloride (0.75 g, 4.1 mmol) was dissolved in 60 ml of an equivolume mixture of methanol and water. Potassium bicarbonate (20 ml, 2M) and N-succinimidyl-3-(4-hydroxyphenyl)propionate (1.07 g, 4.1 mmol) were added, and the solution was stirred for 16 hours. The reaction mixture was extracted with ether/ethyl acetate (12:1) and three times with n-butanol. The butanol extracts were combined, filtered through sodium sulfate, and evaporated leaving a clear oil. The product (compound 17, Scheme 6, above) was crystallized from ethyl acetate/ether, with the first precipitate discarded. Yield 0.82 g (78%), mp 171°–174° C., analysis ($C_{14}H_{17}N_3O_2 \cdot \frac{1}{2}H_2O$) calculated 63.38% C, 6.71% H, 15.84% N; found 63.38% C, 6.76% H, 15.77% N. Accurate mass: calculated 259.1321, found 259.1322. 3-(4-Hydroxyphenyl)propionyl derivatives of Nτ- and Nα-methylhistamine (compounds 18 and 20, Scheme 7, above) were prepared by similar methods. Accurate mass: calculated 273.1477, found (Nτ-methylhistamine derivative) 273.1459, found (Nα-methylhistamine derivative) 273.1475.

Table 5 shows the reaction yields for pure derivatives and standard amines after derivatization.

Limit of Sensitivity

The detection limits (defined as signal/noise=3) of histamine, Nτ-methylhistamine and Nα-methylhistamine derivatives were 0.1 pmol, 0.2 pmol, and 1 pmol of the pure amines, respectively.

TABLE 5

| | | Studies of Reaction Yield | | |
|---|---|---|---|---|
| | [A] peak height[a] of 100 pmol of pure derivative (n = 4) | [B] peak height[a] of derivative corresponding to 100 pmol of amine (n = 4) | [C] recovery[b] of derivative after cellulose phosphate column (n = 4) | calculated[c] reaction yield |
| histamine | 100 ± 2.9 (Means ± S.D.) | 89.2 ± 0.0 (Means ± S.D.) | 90.0% | 99.1% |
| Nτ—methylhistamine | 100 ± 1.3 | 83.9 ± 0.9 | 88.4% | 94.9% |
| Nκ—methylhistamine | 100 ± 2.9 | 86.7 ± 1.6 | 88.3% | 98.2% |

[a]Figures indicate relative peak heights (mean peak height of pure derivative of each amine is expressed as 100)
[b]Mean recovery of 100 pmol of pure derivative after cellulose phosphate fibrous cation-exchanger
[c]Reaction yield = $\frac{[B]}{[A]} \times \frac{100}{[C]} \times 100\%$

Brain Tissue Assay

Recovery tests were run as follows: eight rat hypothalami were homogenized with 8 ml of 3% perchloric acid and centrifuged. Internal standard (Nα-methylhistamine) was added to the supernatant and divided into 8 aliquots, 750 microliters each. To each of 4 aliquots, 100 pmol of histamine and Nτ-methylhistamine were added. Then all samples were prepurified with a Dowex 50 W column and derivatized. 96% and 86% recoveries of histamine and Nτ-methylhistamine were obtained, respectively. Coefficients of variation for hypothalamic histamine, Nτ-methylhistamine and internal standard obtained from the native tissue were 4.6%, 5.2% and 3.8%, respectively (average of four repetitions). Due to the high sensitivity and precision of this method the measurement of histamine and Nτ-methylhistamine in single nuclei of rat hypothalamus was possible. The results are shown in Table 6. Mean histamine and N$\tau$-methylhistamine contents of the median eminence (1.5±0.3 (standard deviation (SD)) mg tissue, average of five repetitions) were 3.7±1.0 and 1.5±0.4 (SD) pmol/g tissue, respectively. This histamine concentration is in areement with previous reports using a radioenzymatic assay.

TABLE 6

Histamine and N$^\tau$—methylhistamine Contents in Rat Hypothalamus

| | N | Content (Mean ± SD) |
|---|---|---|
| histamine | 7 | 3.01 ± 0.51 nmol/g (335 ± 57 ng/g) |
| N$^\tau$—methylhistamine | 7 | 0.86 ± 0.14 nmol/g (108 ± 18 ng/g) |

EXAMPLE 3

β-Phenylethylamine

β-Phenylethylamine is derivatized with Bolton-Hunter reagent as follows. β-Phenylethylamine and Bolton-Hunter reagent were mixed in equimolar quantities in a 1:1 solution of methanol and sodium phosphate buffer (1M, pH 8). After 30 minutes, an excess of water was added. A crystalline solid was collected, washed with water and dried in vacuo giving 1-[3-(4-hydroxyphenyl)-propionylamino]-2-(phenyl) ethane in 75% yield.

As internal standard, 1-[3-(4-hydroxyphenyl)-propionylamino]-2-(4-methylphenyl) ethane was prepared by the same method as above from β-tolylethylamine and Bolton-Hunter reagent. The product was isolated in 89% yield.

A brain tissue sample prepared by the same method described in Example 2 is reacted with sulfo B-H at pH 10. Following the reaction the mixture is extracted with ethyl acetate. The ethyl acetate is evaporated and the residue reconstituted and applied to HPLC as described in Example 1.

The retention time in the HPLC column for the pure phenylethylamine derivative is 5.00 minutes and its molecular weight, as determined by mass spectroscopy is 270. For the internal standard, the retention time is 7.98 minutes and its as determined by mass spectroscopy 284. HPLC conditions are the same as those shown in Table 7.

EXAMPLES 4–7

Other Amines

To show the general applicability of the present invention, pure samples of the other amines shown in Table 7 were derivatized with sulfo B-H and extracted into ethyl acetate. The results after HLPC are shown in Table 7.

TABLE 7

| Example | Derivative of structure | mass spec | retention time (min) |
|---|---|---|---|
| 4 | tuamine | 263 | 12.25 |
| 5 | wyamine | 312 | 8.08 |
| 6 | tranylcypromine | 282 | 6.00 |
| 7 | tryptamine | 315 | 4.35 | column: Phenomenex, Ultrex-C$_8$, 3u, 10 cm × 4.6 mm.
mobile phase: 48% MeOH/0.14 M sodium acetate, pH 4
flow: 0.9 ml/min, 4100 psi.

It is understood that the present invention is not limited to the embodiments disclosed which are illustratively offered and that modifications may be made without departing from the invention.

What is claimed is:

1. A process for the quantitative detection of amines in a fluid sample, comprising:
    reacting a fluid sample, under a non-reactive atmosphere, with a reactive O-acyl N-hydroxysulfosuccinamide to form an N-acylated derivative of the amine to be detected, wherein said acyl group is selected so as to enhance the separability of said N-acylated amine derivative from polar substances in the remainder of the fluid which may interfere with electrochemical measuring;
    separating the N-acylated amine derivative from polar substances in the remainder of the fluid sample which may interfere with electrochemical measuring; and
    subjecting the separating N-acylated amine derivative to electrochemical detection coupled to high pressure liquid chromatography.

2. A process in accordance with claim 1, wherein said fluid sample is a biological fluid.

3. A process in accordance with claim 1, wherein the acyl group of said reactive O-acyl N-hydroxysulfosuccinamide is selected so as to render said N-acylated amine derivative soluble in an organic solvent, and said separating step comprises extracting the N-acylated amine derivative with a suitable organic solvent.

4. A process in accordance with claim 1, wherein the acyl group of said reactive O-acyl hydroxysulfosuccinamide is selected so as to render said N-acylated amine derivative isolatable by chromatography from polar substances in the remainder of the fluid sample which may interfere with electrochemical measuring, and said separating step is achieved by chromatography.

5. A process in accordance with claim 1 wherein said reactive O-acyl N-hydroxysulfosuccinamide in water soluble.

6. In the process for the quantitative detection of electroactive amines in an aqueous fluid sample containing other polar substances, comprising electrochemical detection coupled to high pressure liquid chromatography, the improvement whereby the sensitivity of such process can be substantially increased, comprising the steps of, prior to said detection step:
    reacting the fluid sample, under a non-reactive atmosphere, with a reactive O-acyl hydroxlamine derivative to form an N-acylated derivative of the electroactive amine to be detected, wherein said reactive O-acyl hydroxylamine derivative is selected to have the property that it is not reactive toward the portion of the electroactive amine to be detected which renders the amine electroactive, and wherein said acyl group is selected so as to render said N-acylated amine derivative soluble in an organic solvent and thereby separable from polar substances in the remainder of the fluid which may interfere with electrochemical measuring; and
    separating the N-acylated amine derivative from polar substances in the remainder of the fluid sample which may interfere with electrochemical measuring by extracting the N-acylated amine derivative with a suitable organic solvent.

7. A process in accordance with claim 6, further including the step of concentrating the derivative-containing organic solvent solution obtained by said separating step by evaporating a portion of said solvent prior to said detection step.

8. A process in accordance with claim 6, wherein said O-acyl hydroxylamine derivative is an ester of N-hydroxysuccinamide or an ester of an N-hydroxysulfosuccinamide.

9. A process in accordance with claim 8, wherein said O-acyl hydroxylamine derivative is a compound of the formula

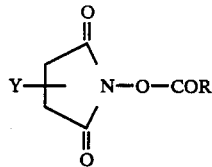

wherein R represents a straight chain alkyl group, a parasubstituted phenol, a hydroquinone, an aniline homolog, an aniline analog, a thiol, an oxidizable thioether, a quinone, a nitroaromatic, a disulfide or —$CH_2NHCONH_2$, and Y is —H or —$SO_3$.

10. A process in accordance with claim 9, wherein R is —$CH_3$, —$CH_2CH_3$, —$CH_2NHCONH_2$ or

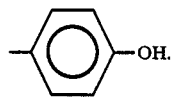

11. A process in accordance with claim 6, wherein said O-acyl hydroxylamine derivative is an ester of N-hydroxysulfosuccinamide.

12. A process in accordance with claim 11, wherein said ester of N-hydroxysulfosuccinamide is water soluble.

13. A process in accordance with claim 6, further including the steps of adding to the fluid sample, prior to said reacting step, a known quantity of an analog or homolog of said electroactive amine having essentially the same reactivity as said amine towards said O-acyl hydroxylamine derivative, thereby serving as an internal standard.

14. A process in accordance with claim 13, wherein the fluid of said fluid sample is a biological fluid.

15. A process in accordance with claim 6, wherein the fluid of said fluid sample is a biological fluid.

16. In the process for the quantitative detection of non-electroactive amines in an aqueous fluid sample containing other polar substances, comprising derivatizing said amines with an electroactive group and detecting said derivatized amine by electrochemical detection coupled to high pressure liquid chromatography, the improvement whereby such non-electroactive amines can be quantitatively detected in the fluid sample at substantial sensitivity, comprising the steps of, prior to said detecting step:

reacting the fluid sample, under a non-reactive atmosphere, with a reactive O-acyl hydroxylamine derivative to form an N-acylated derivative of the non-electroactive amine to be detected, wherein said reactive O-acyl hydroxlamine derivative is selected to have the property that it is not reactive toward hydroxyl groups, and wherein said acyl group is selected so as to render said N-acylated amine derivative soluble in an organic solvent and thereby separable from polar substances in the remainder of the fluid sample which may interfere with electrochemical measuring and to render said N-acylated amine derivative electroactive; and separating the N-acylated amine derivative from polar substances in the remainder of the fluid sample which may interfere with electrochemical measuring by extracting the N-acylated amine derivative with a suitable organic solvent.

17. A process in accordance with claim 16, further including the step of concentrating the derivative-containing organic solvent solution obtained by said separating step by evaporating a portion of said solvent prior to said detection step.

18. A process in accordance with claim 16, wherein said O-acyl hydroxylamine derivative is an ester of N-hydroxysuccinamide or an ester of an N-hydroxysulfosuccinamide.

19. A process in accordance with claim 18, wherein said O-acyl hydroxylamine derivative is a compound of the formula

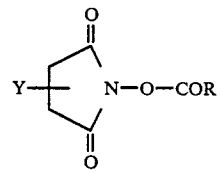

wherein R represents a straight chain alkyl group, a parasubstituted phenol, a hydroquinone, an aniline homolog, an aniline analog, a thiol, an oxidizable thioether, a quinone, a nitroaromatic, a disulfide or —$CH_2NHCONH_2$, and Y is —H or —$SO_3$.

20. A process in accordance with claim 19, wherein R is —$CH_3$, —$CH_2CH_3$, —$CH_2NHCONH_2$ or

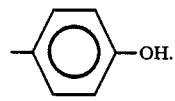

21. A process in accordance with claim 16, wherein said O-acyl hydroxylamine derivative is an ester of N-hydroxysulfosuccinamide.

22. A process in accordance with claim 21, wherein said ester of N-hydroxysulfosuccinamide is water soluble.

23. A process in accordance with claim 16, further including the steps of adding to the fluid sample, prior to said reacting step, a known quantity of an analog or homolog of said non-electroactive amine having essentially the same reactivity as said amine towards said O-acyl hydroxylamine derivative, thereby serving as an internal standard.

24. A process in accordance with claim 23, wherein the fluid of said fluid sample is a biological fluid.

25. A process in accordance with claim 16, wherein the fluid of said fluid sample is a biological fluid.

* * * * *